(12) United States Patent
Coller et al.

(10) Patent No.: US 11,236,345 B2
(45) Date of Patent: *Feb. 1, 2022

(54) METHODS OF MODULATING NUCLEIC ACID STABILITY AND PROTEIN EXPRESSION

(71) Applicant: CASE WESTERN RESERVE UNIVERSITY, Cleveland, OH (US)

(72) Inventors: Jeffery M. Coller, Novelty, OH (US); Kristian E. Baker, Novelty, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/557,412

(22) PCT Filed: Mar. 9, 2016

(86) PCT No.: PCT/US2016/021594
§ 371 (c)(1),
(2) Date: Sep. 11, 2017

(87) PCT Pub. No.: WO2016/145101
PCT Pub. Date: Sep. 15, 2016

(65) Prior Publication Data
US 2018/0112226 A1 Apr. 26, 2018

Related U.S. Application Data

(60) Provisional application No. 62/130,398, filed on Mar. 9, 2015.

(51) Int. Cl.
*C12N 15/68* (2006.01)
*C12N 15/81* (2006.01)
*C12N 15/67* (2006.01)
*C12P 21/02* (2006.01)
*C12N 15/85* (2006.01)

(52) U.S. Cl.
CPC ............. *C12N 15/68* (2013.01); *C12N 15/67* (2013.01); *C12N 15/81* (2013.01); *C12N 15/85* (2013.01); *C12P 21/02* (2013.01); *C12N 2800/22* (2013.01)

(58) Field of Classification Search
None
See application file for complete search history.

(56) References Cited

PUBLICATIONS

Koresawa et al., "Synthesis of a New Cre Recombinase Gene Based on Optimal Codon Usage for Mammalian Systems" 127 Journal of Biochemistry 367-372 (2000).*
Murray et al., "Codon usage in plant genes" 17(2) Nucleic Acids Research 477-498 (1989).*
Sinclair, Graham, et al., "Synonymous codon usage bias and the expression of human glucocerebrosidase– in the methylotrophic yeast, Pichia pastoris", Protein Expression and Purification 26 (2002) 96-105.

* cited by examiner

*Primary Examiner* — Nancy J Leith
(74) *Attorney, Agent, or Firm* — Tarolli, Sundheim, Covell & Tummino LLP

(57) ABSTRACT

A synthetic nucleic acid which encodes a protein wherein at least one optimal or non-optimal codon in a wild type nucleic acid encoding the protein has been replaced respectively with one or more non-optimal codons or optimal codons encoding the same amino acid.

16 Claims, 7 Drawing Sheets

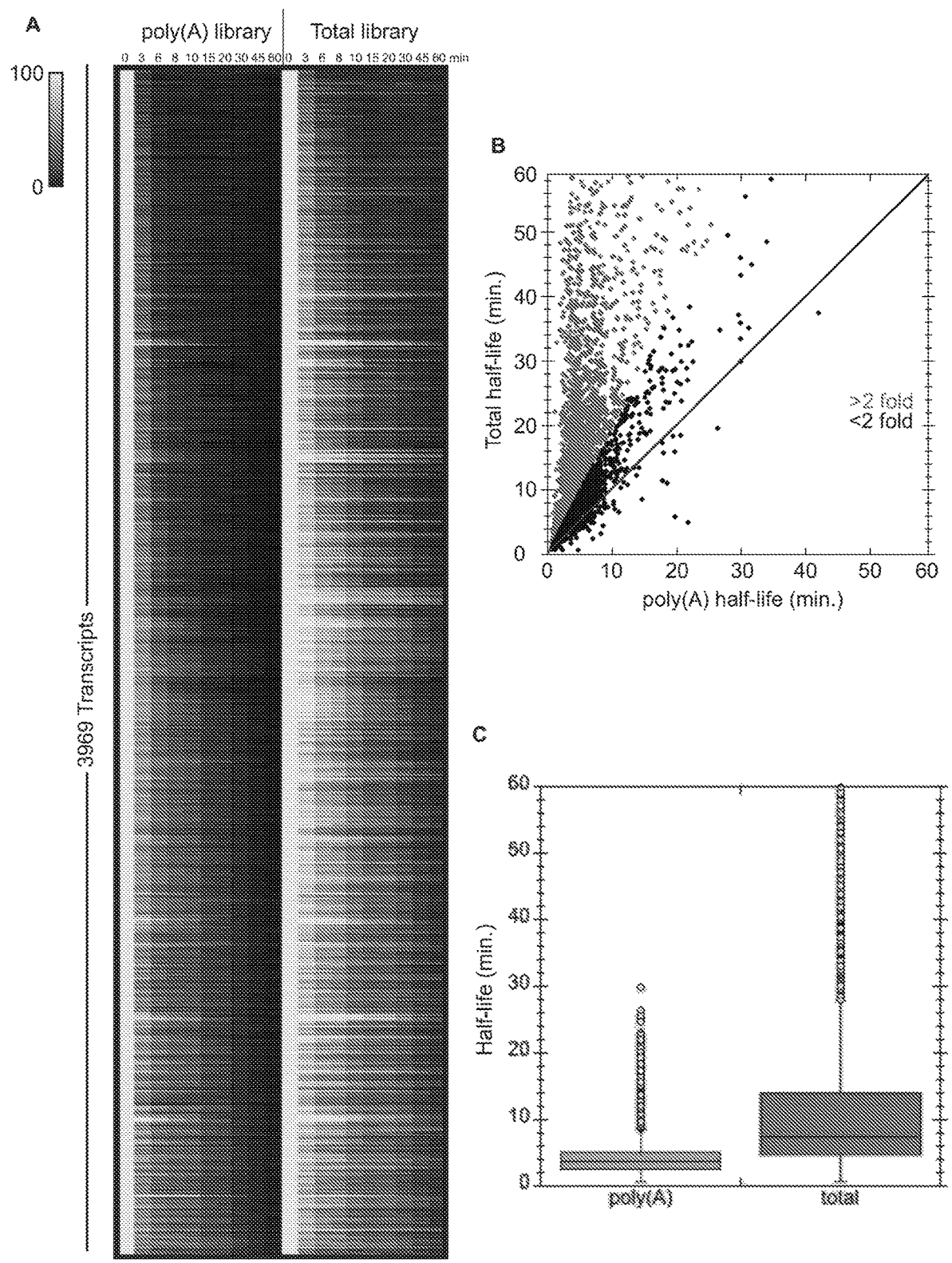
Figs. 1A-C

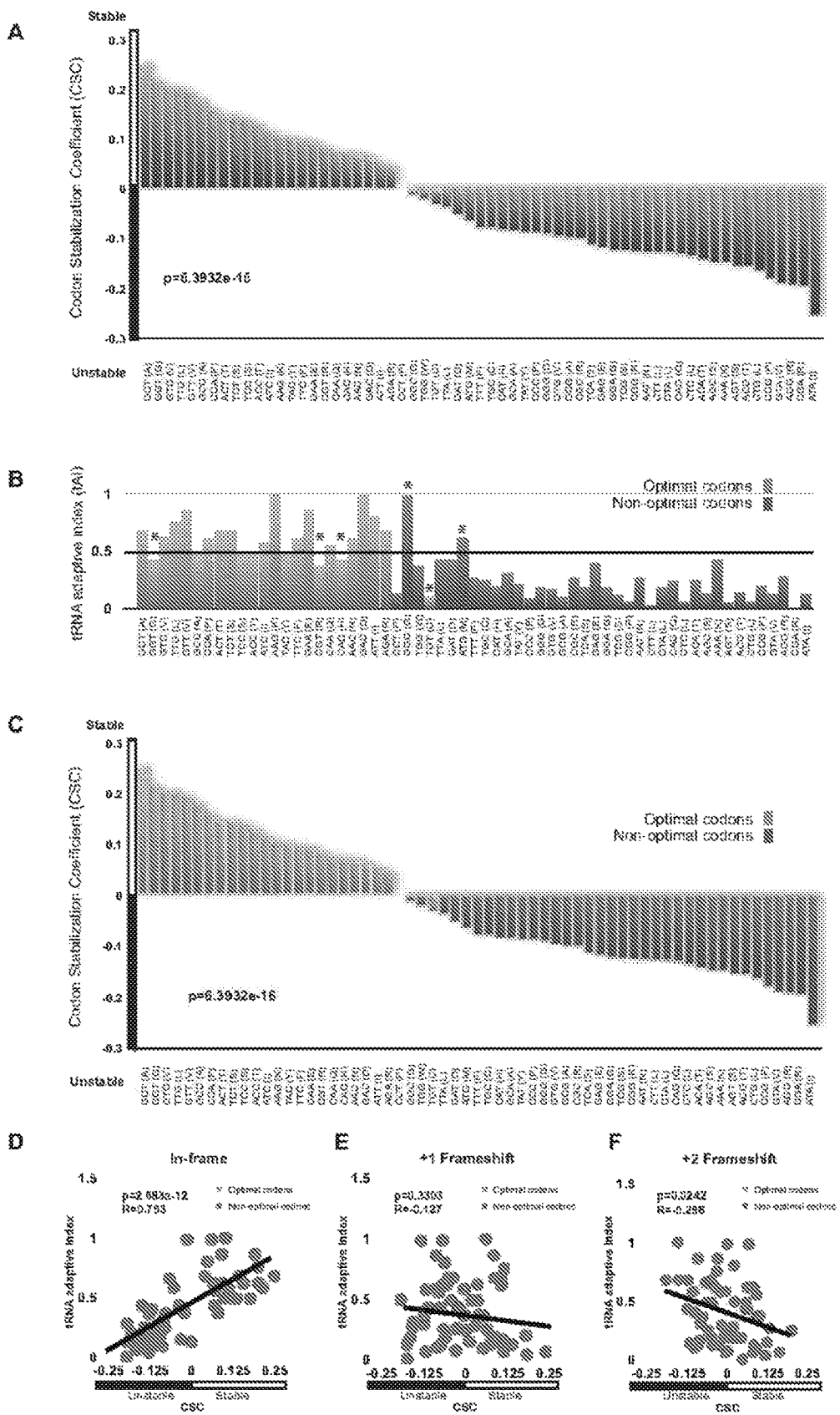
Figs. 2A-F

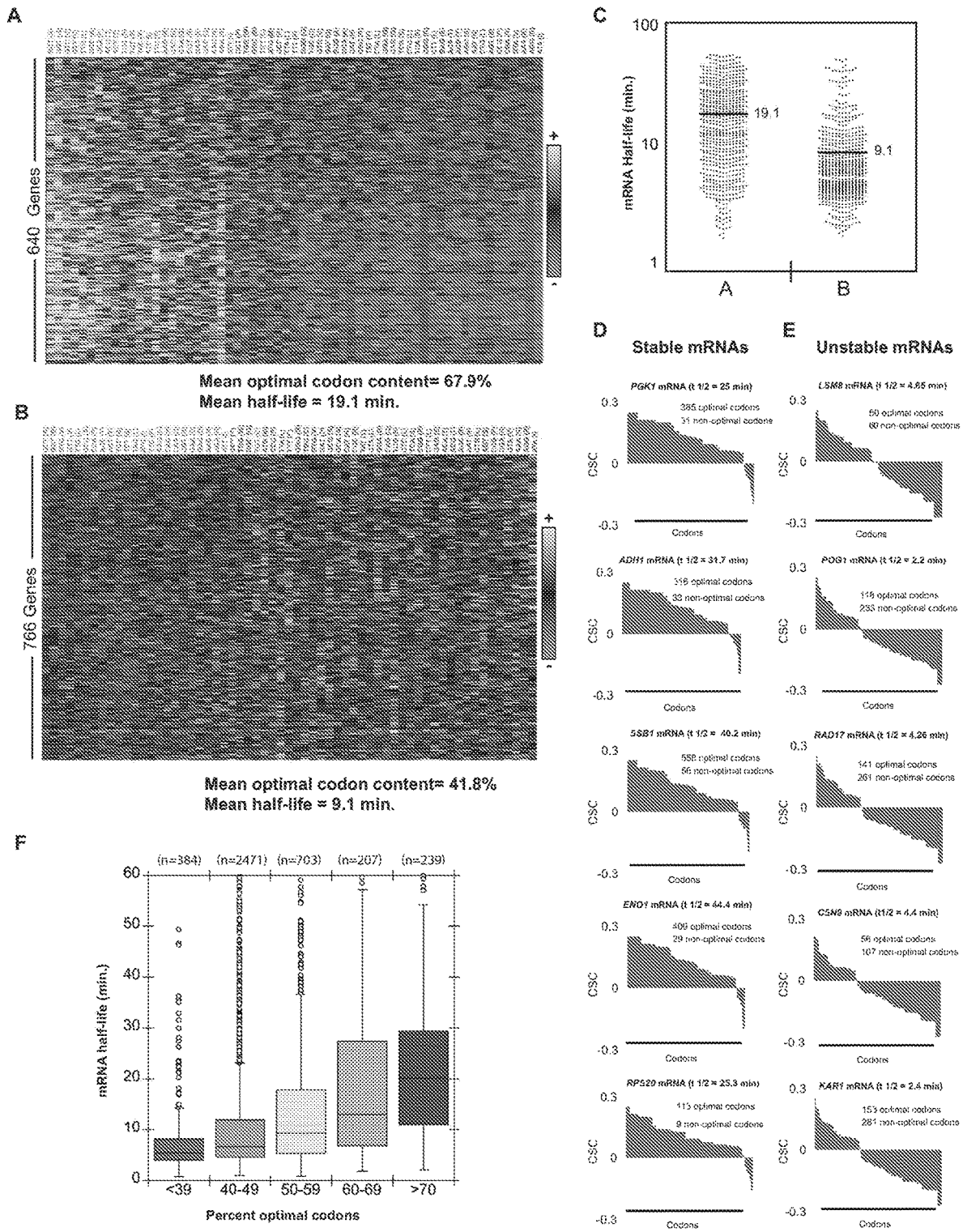
Figs. 3A-F

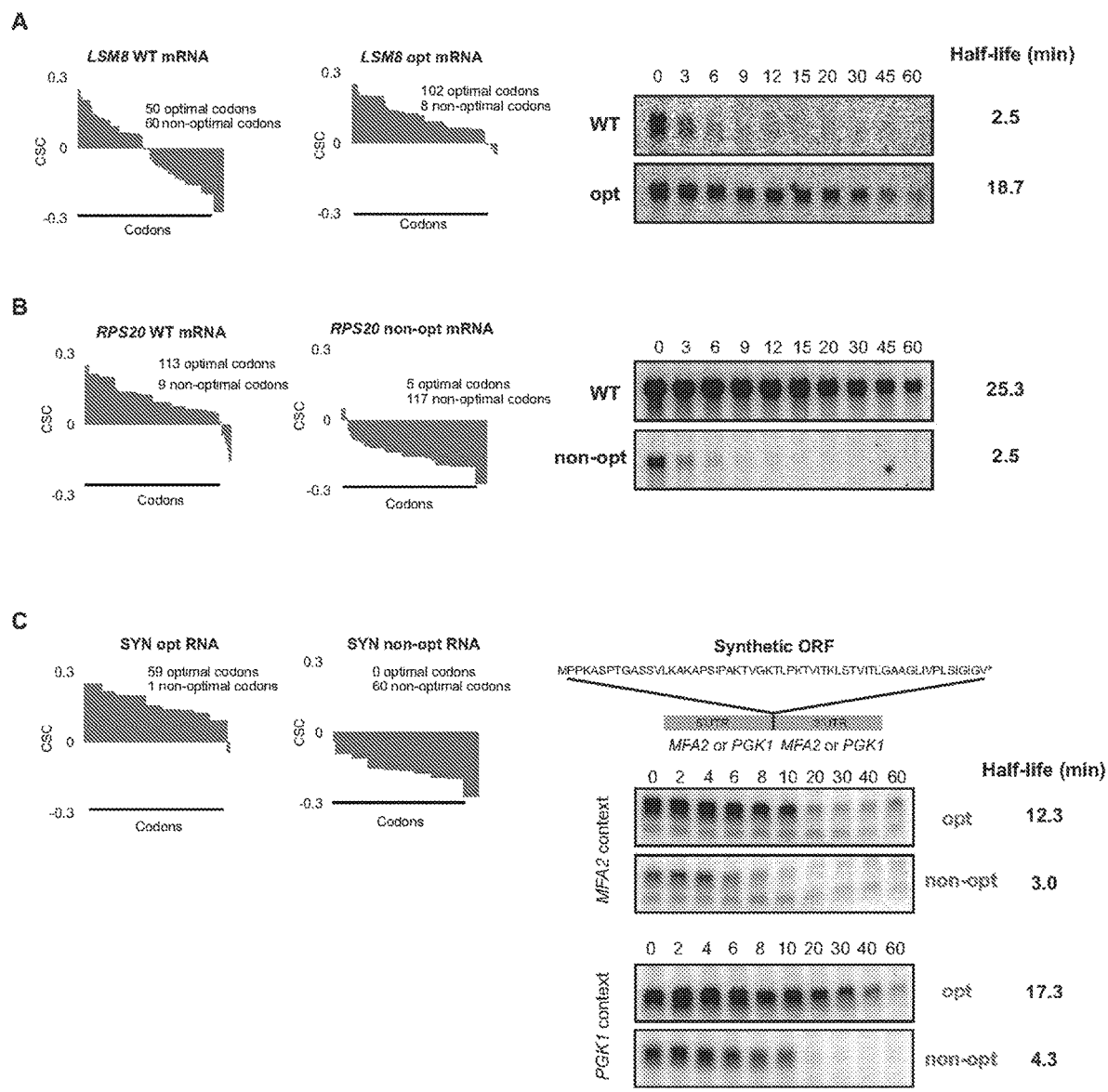
Figs. 4A-C

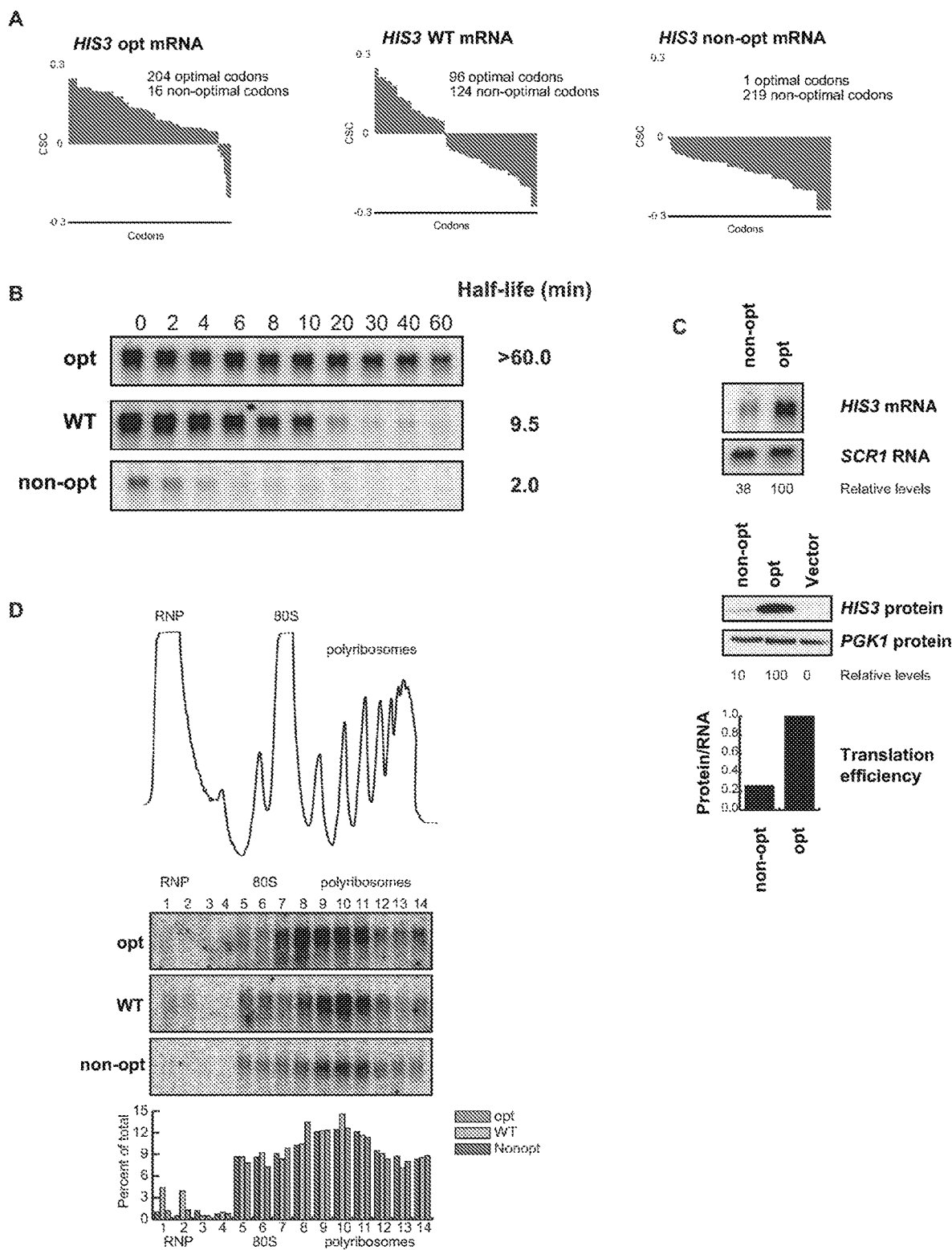
Figs. 5A-D

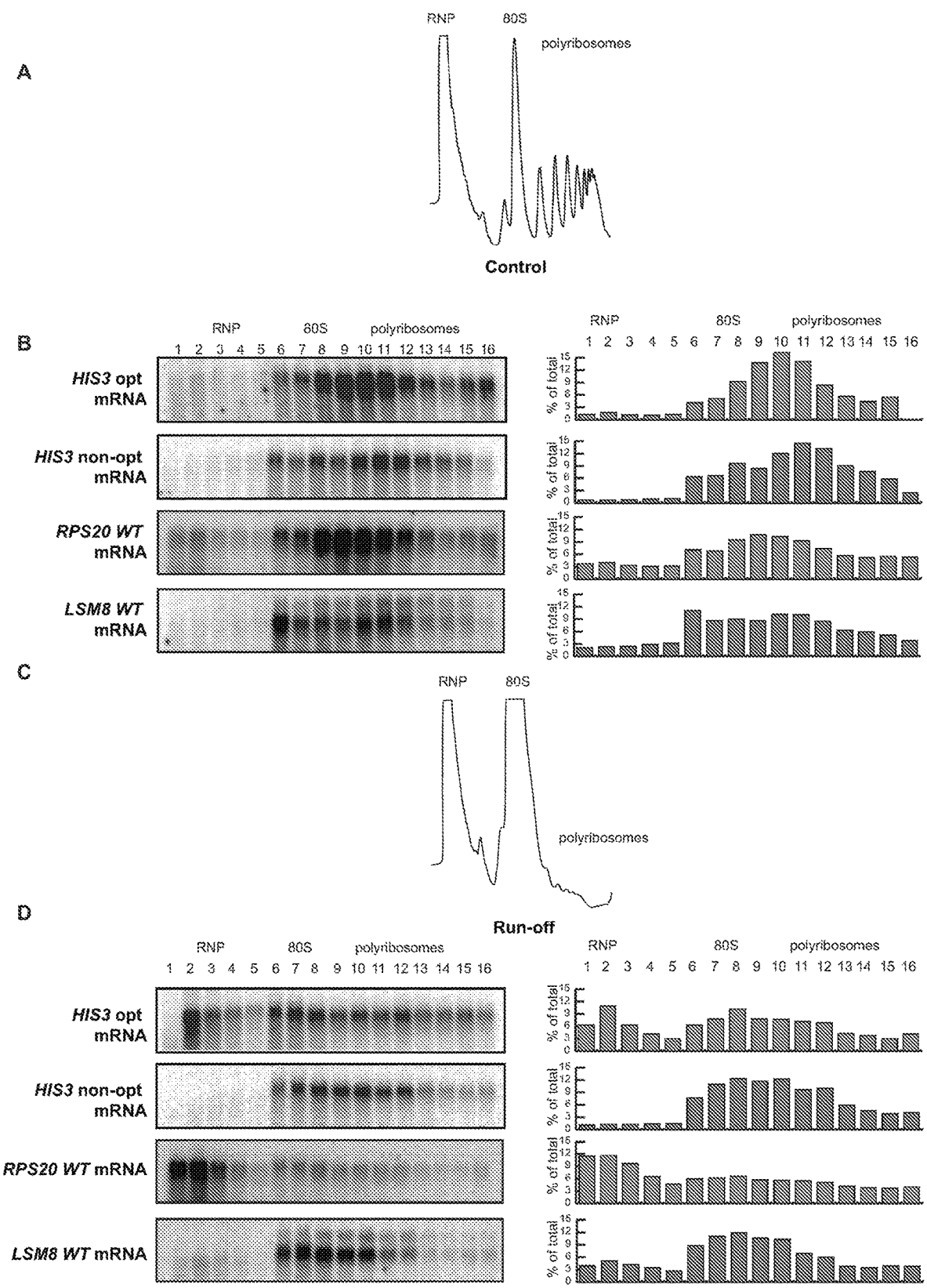
Figs. 6A-D

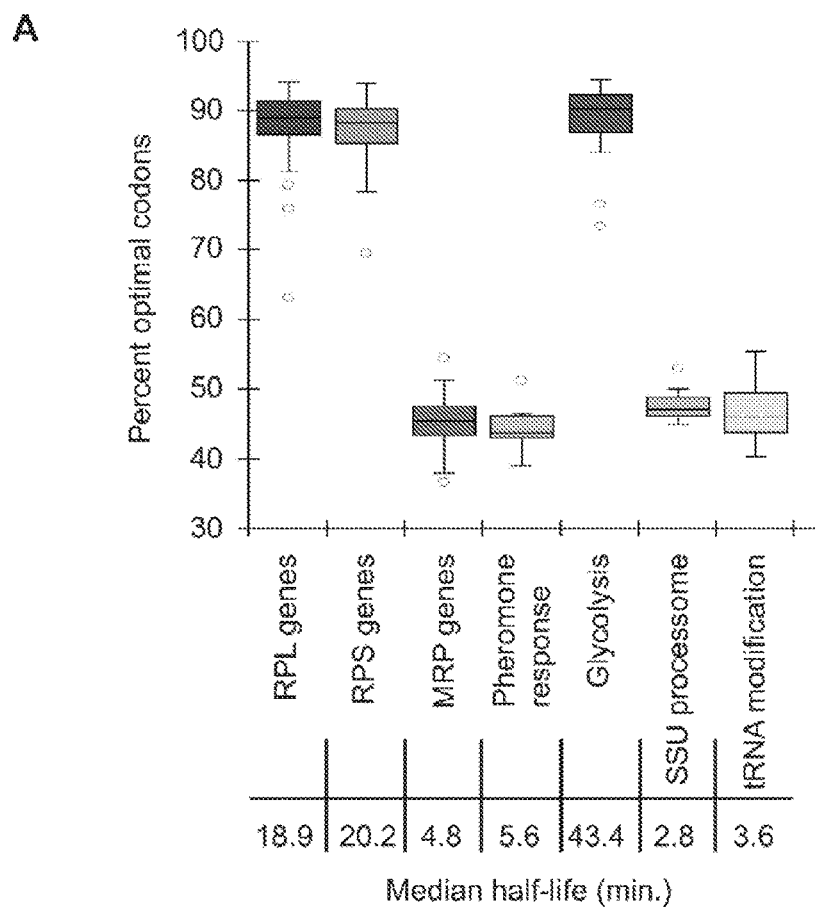
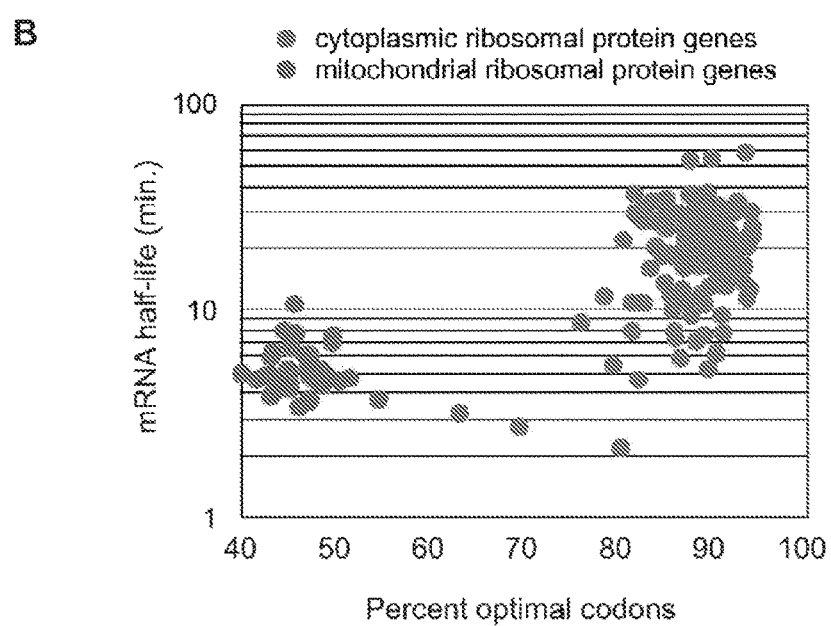
Figs. 7A-B

METHODS OF MODULATING NUCLEIC ACID STABILITY AND PROTEIN EXPRESSION

RELATED APPLICATION

This application claims priority from U.S. Provisional Application No. 62/130,398, filed Mar. 9, 2015, the subject matter of which is incorporated herein by reference in its entirety.

GOVERNMENT FUNDING

This invention was made with government support under Grant No. GM080465 awarded by The National Institute of Health. The United States government has certain rights to the invention.

BACKGROUND

All life forms use 61 codons to translate genetic information encoded within DNA (and RNA) into protein sequence. These codons are the "signals" used by the cell to dictate the accurate incorporation of individual amino acids (1 from a possible 20) into the growing polypeptide chain during the process of translation. Since there are 61 codons and only 20 amino acids, redundancy exists within the genetic code and the incorporation of a single amino acid can be dictated by more than one codon triplet (i.e., synonymous codons—different codon triplets directing the incorporation of the same amino acid into protein).

Messenger RNA (mRNA) degradation plays a role in regulating transcript levels in the cell and is a major control point for modulating gene expression. Degradation of most mRNAs in *Saccharomyces cerevisiae* is initiated by removal of the 3' poly(A) tail (deadenylation), followed by cleavage of the 5' 7 mGpppN cap (decapping) and exonucleolytic degradation of the mRNA body in a 5'-3' direction. Despite being targeted by a common decay pathway, turnover rates for individual yeast mRNAs differ dramatically with half-lives ranging from <1 minute to 60 minutes or greater. RNA features that influence transcript stability have long been sought, and some sequence and/or structural elements located within 5' and 3' untranslated regions (UTRs) have been implicated in contributing to the decay of a subset of mRNAs. However, these features regulate mRNA stability predominantly in a transcript-specific manner through binding of regulatory factors and cannot account for the wide variation in half-lives observed across the entire transcriptome. Therefore, it seems likely that additional and more general features which act to modulate transcript stability could exist within mRNAs.

SUMMARY

Embodiments described herein relate to methods of modulating nucleic acid stability and protein expression by codon modification of wild type or native nucleic acids as well as to synthetic nucleic acids sequences formed by such codon modifications. In some embodiments, at least one optimal or non-optimal codon in a wild type nucleic acid sequence encoding a protein can be replaced respectively with one or more non-optimal codons or optimal codons encoding the same amino acid. The synthetic nucleic acid sequence with such modification(s) is capable of expressing the protein at a level that is at least about 10% different (e.g., greater or less) compared to that expressed by the wild type or native nucleic acid sequence in an in vitro mammalian cell culture system under identical conditions. The optimal codons are selected from the group consisting of gct (Alanine), ggt (Glycine), gtc (Valine), ttg (Leucine), gtt (Valine), gcc (Alanine), cca (Proline), act (Threonine), tct (Serine), tcc (Serine), acc (Threonine), atc (Isoleucine), aag (Lysine), tac (Tyrosine), ttc (Phenylalanine), gaa (Glutamaic Acid), cgt (Arginine), caa (Glutamine), cac (Histidine), aac (Asparagine), gac (Aspartic Acid), att (Isoleucine), aga (Arginine), and tgt (Cysteine). The non-optimal codons are selected from the group consisting of cct (Proline), ggc (Glycine), tgg (Tryptophan), tta (Leucine), gat (Aspartic Acid), atg (Methionine), ttt (Phenylalanine), tgc (Cysteine), cat (Histidine), gca (Alanine), tat (Tyrosine), ccc (Proline), ggg (Glycine), gtg (Valine), gcg (Alanine), cgc (Arginine), tca (Serine), gag (Glutamaic Acid), gga (Glycine), tcg (Serine), cgg (Arginine), aat (Asparagine), ctt (Leucine), cta (Leucine), cag (Glutamine), ctc (Leucine), aca (Threonine), agc (Serine), aaa (Lysine), agt (Serine), acg (Threonine), ctg (Leucine), ccg (Proline), gta (Valine), agg (Arginine), cga (Arginine), and ata (Isoleucine).

In some embodiments, the synthetic nucleic sequence is capable of expressing the protein at a level which is at least about 20%, about 25%, about 30%, about 40%, about 50%, about 60%, about 70%, about 80%, about 90%, about 100%, or more different compared to that expressed by the wild type or native nucleic acid sequence in an in vitro mammalian cell culture system under identical conditions.

In some embodiments, one or more of the optimal codons of the wild type nucleic acid sequence can replaced with a non-optimal codon encoding the same amino acid as the replaced codon so that the synthetic nucleic acid sequence has less than about 50%, less than about 40%, less than about 30%, less than about 25%, less than about 20%, less than about 10%, or less than about 1% optimal codons. The replacement of the one or more optimal codons from the nucleic acid sequence with a non-optimal codon can decrease stabilization of mRNA transcribed from the nucleic acid sequence compared to the nucleic acid sequence prior to replacement.

In other embodiments one or more of the non-optimal codons is replaced with an optimal codon encoding the same amino acid as the replaced codon so that the synthetic nucleic acid sequence has more than about 50%, more than about 60%, more than about 70%, more than about 75%, more than about 80%, more than about 90%, more than about 95%, or more than about 99% about optimal codons. The replacement of the one or more non-optimal codons from the nucleic acid sequence with optimal codons can increase stabilization of mRNA transcribed from the nucleic acid sequence compared to the nucleic acid sequence prior to replacement.

Other embodiments relate to a method for preparing a synthetic nucleic acid encoding a protein expressed by a eukaryotic cell. The method can include identifying optimal and non-optimal codons in a nucleic acid encoding the protein, and replacing one or more of the optimal codons with a non-optimal codon encoding the same amino acid as the replaced codon or replacing one or more of the non-optimal codons with an optimal codon encoding the same amino acid. The replacement of the one or more codons from the nucleic acid encoding the protein can modulate expression of the protein in the eukaryotic cell at least about 10%, about 20%, about 25%, about 30%, about 40%, about 50%, about 60%, about 70%, about 80%, about 90%, about 100%, or more compared to that expressed by the nucleic acid prior to replacement in an in vitro mammalian cell culture system under identical conditions.

Still other embodiments described herein relate to a method of modulating the expression of a recombinant protein in a host cell. The method can include identifying optimal and non-optimal codons in a nucleic acid sequence that encodes the protein. One or more of the optimal codons can then be replaced with a non-optimal codon encoding the same amino acid as the replaced codon or one or more of the non-optimal codons can be replaced with an optimal codon encoding the same amino acid. The host cell can be transfected with the nucleic acid with the replaced codon. The replacement of the one or more codons from the nucleic acid sequence can modulates expression of the recombinant protein in the host cell at least about 10%, about 20%, about 25%, about 30%, about 40%, about 50%, about 60%, about 70%, about 80%, about 90%, about 100%, or more compared to the nucleic acid sequence prior to replacement.

In some embodiments, the replacement of the one or more codons from the nucleic acid sequence increases expression of the recombinant protein in the host cell at least about 10%, about 20%, about 25%, about 30%, about 40%, about 50%, about 60%, about 70%, about 80%, about 90%, about 100%, or more compared to the nucleic acid sequence prior to replacement.

In other embodiments, the replacement of the one or more codons from the nucleic acid sequence can decrease expression of the recombinant protein in the host cell at least about 10%, at least about 10%, about 20%, about 25%, about 30%, about 40%, about 50%, about 60%, about 70%, about 80%, about 90%, or more compared to the nucleic acid sequence prior to replacement.

BRIEF DESCRIPTION OF THE DRAWINGS

FIGS. 1(A-C) illustrate graphs showing mRNA half-lives calculated from poly(A)+vs total mRNA differ significantly. RNA-seq was performed on poly(A)+ and total RNA libraries prepared from rpb1-1 transcriptional shut-off experiments across a 60 minute time course. (A) All mRNAs with reliable half-lives in both libraries are plotted visually. Color intensity represents normalized mRNA remaining (time 0 is set to 100% for each mRNA). (B) Half-life of each mRNA plotted as calculated from total mRNA sequencing against the poly(A) sequencing. Data points with a >2 fold difference are highlighted in red. (C) Overview of the distribution of half-lives for both libraries.

FIGS. 2(A-F) illustrate plots showing that codon composition correlates with stability. (A) The Codon occurrence to mRNA Stability Correlation coefficient (CSC) plotted for each codon as calculated from the total RNA data set. The CSC is the R-value of the correlation between the occurrences of that codon and the half-lives of mRNA. Overall p-value is 6.3932e−16, permutation p-value is <$10^{-4}$. (B) tRNA Adaptability Index values for each codon plotted in the same order as (A). Codon optimality is coded, using light grey for optimal codons and dark grey for non-optimal codons. Codons designated with an asterisk (*) were called optimal or non-optimal according to additional criteria discussed therein. (C) The Codon occurrence to mRNA Stability Correlation coefficient (CSC) plotted for each codon as in (A), but optimality information presented in (B) is added by color-coding. Light grey color represents optimal codons and dark grey represents non-optimal. (D) tRNA Adaptive Index values plotted vs. CSC when ORFs are considered in-frame. Light grey indicates optimal codons, dark grey indicates non-optimal codons (R=0.7255, p-value is p-value=2.075e−09, permutation p-value <$10^{-4}$) (E) tRNA Adaptive Index values plotted vs. CSC when ORFs are frameshifted by one nucleotide. Green indicates optimal codons, red indicates non-optimal codons. (F) tRNA Adaptive Index values plotted vs. CSC when ORFs are frameshifted by two nucleotides. Light grey indicates optimal codons, dark grey indicates non-optimal codons.

FIGS. 3(A-F) illustrate heat maps (A) and graphs (B-E) showing that multiple codons are enriched in stable and unstable mRNA classes. (A) Heat map of a class of relatively stable mRNAs with similar codon usage. Each column represents the usage of a single codon, with each row representing one mRNA. (B) As (A), but showing a relatively unstable class of mRNAs. (C) Dot plot showing the distribution of half-lives in the mRNA classes shown in (A, B). (D) Codon optimality diagrams in selected stable mRNAs. Genes are broken down and plotted as individual codons. Codons are presented in order of optimality rather than in their natural order. Higher bars represent more optimal codons (CSC on y-axis). Light grey indicates optimal codons, dark grey indicates non-optimal codons. (E) Codon optimality diagrams in selected unstable mRNAs, as in (D). (F) Box plot of mRNAs half-lives separated into optimality groups. Half of the data fall within the boxed section, with the whiskers representing the rest of the data. Data points falling further than 1.5 fold the interquartile distance are considered outliers.

FIGS. 4(A-C) illustrate graphs and northern blots showing that the stability of mRNAs can be controlled by altering codon optimality. (A) Codon optimality diagram of LSM8 (as FIG. 3E), a naturally non-optimal mRNA shown. LSM8 OPT is a synonymously substituted version of LSM8 engineered for higher optimality. Northern blots of rpb1-1 shut-off experiments are shown on the right with half-life of both reporters. Quantitation is normalized to SCR1 loading controls not shown. (B) As (A), except a naturally optimal mRNA, RPS20 (as in FIG. 3D), has been engineered for lower optimality as RPS20 non opt. Northern blots of rpb1-1 shut-off experiments are shown on the right with half-life of both messages. Quantitation is normalized to SCR1 loading controls not shown. (C) Codon optimality diagrams showing a synthetic mRNA (SYN) encoding the polypeptide shown. Peptide is artificially engineered and has no similarity to any known proteins. SYN opt and non-opt were both inserted into flanking regions from a stable transcript (PGK1) and unstable transcript (MFA2). Northern blots on the right show GAL shut-off experiments demonstrating stability of the SYN mRNA in context of the MFA2 and PGK1 flanking sequences. Quantitation is normalized to SCR1 loading controls not shown.

FIGS. 5(A-D) illustrate graphs, plots, and northern blots showing that optimality can affect translation and stability of an mRNA without changes in ribosome association. (A) Codon optimality diagram of HIS3, a transcript with an intermediate half-life, as well as versions engineered with synonymous substitutions to contain higher and lower percent optimal codons, HIS3 opt and HIS3 non-opt respectively. (B) Northern blots of rpb1-1 shut-off experiments are shown with half-lives of all three messages. Quantitation is normalized to SCR1 loading controls not shown. (C) Northern and western blots for steady state concentrations of the optimal and non-optimal versions of HIS3. Loading controls and quantitation are shown below. Translational efficiency is calculated as relative protein levels divided by relative mRNA levels and plotted at the bottom. (D) A trace of sucrose density gradient analysis, along with northern blot analysis of the gradient fractions. The blots show location of the three HIS3 reporters within the gradient. Quantitation for each fraction is shown below.

FIGS. 6(A-D) illustrate plots, graphs, northern blots showing optimal and non-optimal transcripts are retained differently on polysomes. (A) Representative A260 trace of sucrose density gradient analysis demonstrating normal distribution into RNP, 80S, and polyribosome fractions. (B) Distribution of the optimal and non-optimal HIS3 reporters and the RPS20 and LSM8 mRNAs in the sucrose density gradients under normal conditions showing localization primarily in the polyribosome fractions. (C) Representative A260 trace of sucrose density gradient analysis under run-off conditions, showing collapse of the polyribosome fractions. (D) Distribution of the optimal and non-optimal HIS3 reporters and the RPS20 and LSM8 mRNAs under run-off conditions, demonstrating differential relocation.

FIGS. 7(A-B) illustrate graphs showing that functionally related genes display similar optimality. (A) Groups of genes whose protein products have related functions are plotted to show their optimality. Half of the data fall within the boxed section, with the whiskers representing the rest of the data. Data points falling further than 1.5 fold the interquartile distance are considered outliers. Represented gene groups are: 70 RPL (large ribosomal subunit proteins) genes, 54 RPS (small ribosomal subunit proteins) genes, 42 MRP (mitochondrial ribosomal proteins) genes, 14 pheromone response genes, 10 glycolysis enzymes, 15 SSU (small subunit processosome) genes, 12 tRNA processing genes. (B) Breakdown of two groups to show relationship between optimal codon content and halflife within the groups. mRNA half-life for each protein in the cytoplasmic ribosome and the mitochondrial ribosome is plotted against the optimal codon content of that mRNA.

DETAILED DESCRIPTION

Methods involving conventional molecular biology techniques are described herein. Such techniques are generally known in the art and are described in detail in methodology treatises, such as *Current Protocols in Molecular Biology*, ed. Ausubel et al., Greene Publishing and Wiley-Interscience, New York, 1992 (with periodic updates). Unless otherwise defined, all technical terms used herein have the same meaning as commonly understood by one of ordinary skill in the art to which the present application pertains. Commonly understood definitions of molecular biology terms can be found in, for example, Lodish et al., *Molecular Cell Biology*, 6th Edition, W. H. Freeman: New York, 2007, and Lewin, *Genes IX*, Jones and Bartlett Publishers: Mass., 2008. For convenience, certain terms employed in the specification, examples, and appended claims are collected here.

As used herein, "one or more of a, b, and c" means a, b, c, ab, ac, bc, or abc. The use of "or" herein is the inclusive or.

As used herein, "protein" is a polymer consisting of the 20 amino acids. Although "polypeptide" is often used in reference to relatively large polypeptides, and "peptide" is often used in reference to small polypeptides, usage of these terms in the art overlaps and is varied.

The terms "polynucleotide sequence", "nucleic acid sequence", and "nucleotide sequence" are also used interchangeably herein.

"Recombinant," as used herein, means that a protein is derived from a prokaryotic or eukaryotic expression system.

The term "wild type" refers to the naturally-occurring polynucleotide sequence encoding a protein, or a portion thereof, or protein sequence, or portion thereof, respectively, as it normally exists in vivo.

As used herein, the term "nucleic acid" refers to polynucleotides, such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

As used herein, the term "gene" or "recombinant gene" refers to a nucleic acid comprising an open reading frame encoding a polypeptide, including both exon and (optionally) intron sequences.

As used herein, the term "vector" refers to a nucleic acid molecule capable of transporting another nucleic acid to which it has been linked. Preferred vectors are those capable of one or more of, autonomous replication and expression of nucleic acids to which they are linked. Vectors capable of directing the expression of genes to which they are operatively linked are referred to herein as "expression vectors".

A polynucleotide sequence (DNA, RNA) is "operatively linked" to an expression control sequence when the expression control sequence controls and regulates the transcription and translation of that polynucleotide sequence. The term "operatively linked" includes having an appropriate start signal (e.g., ATG) in front of the polynucleotide sequence to be expressed, and maintaining the correct reading frame to permit expression of the polynucleotide sequence under the control of the expression control sequence, and production of the desired polypeptide encoded by the polynucleotide sequence.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA" or "mRNA" refers to the RNA that is without introns and that can be translated into protein by the cell. "cDNA" refers to a double-stranded DNA that is complementary to, and derived from, mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065; WO 99/28508). The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated and yet has an effect on cellular processes. The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment(s) of the invention. Expression may also refer to translation of mRNA into a polypeptide.

"Transcriptional regulatory sequence" is a generic term used throughout the specification to refer to nucleic acid sequences, such as initiation signals, enhancers, and promoters, which induce or control transcription of protein coding sequences with which they are operably linked. In some examples, transcription of a recombinant gene is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences, which control transcription of the naturally occurring form of a protein.

"Homology" and "identity" are used synonymously throughout and refer to sequence similarity between two peptides or between two nucleic acid molecules. Homology can be determined by comparing a position in each sequence, which may be aligned for purposes of comparison. When a position in the compared sequence is occupied by the same base or amino acid, then the molecules are homologous or identical at that position. A degree of homology or identity between sequences is a function of the number of matching or homologous positions shared by the sequences.

The term "isolated" as used herein with respect to nucleic acids, such as DNA or RNA, refers to molecules separated from other DNAs, or RNAs, respectively, which are present in the natural source of the macromolecule. The term isolated as used herein also refers to a nucleic acid or peptide that is substantially free of cellular material or culture medium when produced by recombinant DNA techniques, or chemical precursors or other chemicals when chemically synthesized. Moreover, an "isolated nucleic acid" is meant to include nucleic acid fragments, which are not naturally occurring as fragments and would not be found in the natural state.

As used herein, the term "in vitro" refers to an artificial environment and to processes or reactions that occur within an artificial environment. In vitro environments consist of, but are not limited to, test tubes and cell culture. The term "in vivo" refers to the natural environment (e.g., an animal or a cell) and to processes or reaction that occur within a natural environment.

As used herein, the term "synthetic" as used herein can be in reference to a nucleotide sequence (or nucleic acid molecule comprising a synthetic nucleotide sequence), the term "synthetic" refers to a sequence that is designed (e.g., in silico), for example, for the purpose of expressing an encoded polypeptide of interest. The term "synthetic nucleotide" also includes the product of the manufacture of a nucleic acid molecule by means of chemically synthesized oligonucleotides by in vitro or in vivo methodologies known to those skilled in the art of gene synthesis, or by combinations of in vitro or in vivo methods.

As used herein, the term "mammalian" refers to any mammal, including a human being.

Embodiments described herein relate to methods of modulating nucleic acid stability and protein expression by codon modification of wild type or native nucleic acids encoding proteins or open reading frames or protein coding regions of nucleic acid sequences as well as to synthetic nucleic acids sequences formed by such codon modifications.

It was found that synonymous codon triplets are not recognized by cells identically and that mRNAs enriched in triplets which are deemed 'optimal' (see below) are translated more efficiently, have greater stability, and express higher protein levels than mRNA counterparts which lack optimal codons. Codon optimality represents an established scale that reflects the balance between the supply of charged tRNA molecules for a particular codon in the cytoplasmic pool and the demand imposed by the codon as it is read by the translating ribosomes. Codon optimality, therefore, represents a measure of translation efficiency and mRNAs enriched in optimal codons are decoded faster and more accurately by the ribosome than non-optimal codons which slow translation elongation. Not only does codon optimality modulate translation elongation rate, but it also dramatically impacts mRNA stability and protein output from that mRNA template. Codon optimality therefore impinges greatly on gene expression by modulating the level of protein product both through impacting mRNA decay and translational elongation rates. Substitution of optimal codons with synonymous, non-optimal codons results in dramatic mRNA destabilization and slowed translational elongation, while the converse substitution significantly increases stability and protein synthesis. Advantageously, the substitution of codons in mRNA protein coding regions and the consequential impact on gene expression does not alter the identity of the polypeptide/protein product.

In accordance with embodiments described herein, transcript-specific translation elongation rate, as dictated by codon triplet usage, can be predictably manipulated to achieve a vast array of mRNA stabilities and protein levels. Since codon optimality is achieved through tRNA concentrations, cellular tRNA levels and or tRNA modifications can be modulated to predictably alter mRNA and protein abundance. Manipulation of codon usage can be used for protein engineering and large-scale protein expression as well as a means to achieve desired therapeutic effects by altering protein expression levels without altering protein sequence.

Optimal and non-optimal codons as defined herein were designated by determining if mRNAs enriched in any individual codon demonstrated greater or lesser stability. For purposes of this application, mRNAs were defined as stable if they have a half-life greater than 2-fold longer than the average (e.g., about 20 minutes), and unstable if they have a half-life less than half of the average (e.g., about 5 min). For each codon, a correlation between the frequency of occurrence of that codon in mRNAs and the stabilities of the mRNAs was calculated. Occurrences of a codon were compared to the half-life for each mRNA and a Pearson correlation calculation was used to generate an R-value. This metric is referred to as the Codon occurrence to mRNA Stability Correlation coefficient (CSC). The CSC values for all codons were then compared to each other (FIG. 2A). Strikingly, it was observed that some codons preferentially occurred in stable mRNAs while others occurred preferentially in unstable mRNAs (overall p-value=1.496e−14, permutation p-value <$10^{-4}$). For example, the GCT alanine codon was highly enriched in stable transcripts as defined by RNA-seq analysis, while its synonymous codons, GCG and GCA were preferentially present in unstable transcripts (FIG. 2A). Approximately one-third of all codon triplets were over-represented in stable mRNAs, while the remaining two-thirds appeared to predominate in unstable mRNAs Optimal codons include gct (Alanine), ggt (Glycine), gtc (Valine), ttg (Leucine), gtt (Valine), gcc (Alanine), cca (Proline), act (Threonine), tct (Serine), tcc (Serine), acc (Threonine), atc (Isoleucine), aag (Lysine), tac (Tyrosine), ttc (Phenylalanine), gaa (Glutamaic Acid), cgt (Arginine), caa (Glutamine), cac (Histidine), aac (Asparagine), gac (Aspartic Acid), att (Isoleucine), aga (Arginine), and tgt (Cysteine).

Non-optimal codons include cct (Proline), ggc (Glycine), tgg (Tryptophan), tta (Leucine), gat (Aspartic Acid), atg (Methionine), ttt (Phenylalanine), tgc (Cysteine), cat (Histidine), gca (Alanine), tat (Tyrosine), ccc (Proline), ggg (Glycine), gtg (Valine), gcg (Alanine), cgc (Arginine), tca (Serine), gag (Glutamaic Acid), gga (Glycine), tcg (Serine), cgg (Arginine), aat (Asparagine), ctt (Leucine), cta (Leucine), cag (Glutamine), ctc (Leucine), aca (Threonine), agc (Serine), aaa (Lysine), agt (Serine), acg (Threonine), ctg (Leucine), ccg (Proline), gta (Valine), agg (Arginine), cga (Arginine), and ata (Isoleucine).

In some embodiments, at least one optimal or non-optimal codon in a wild type or native nucleic acid sequence encoding a protein can be synonymously substituted or replaced respectively with one or more non-optimal codons or optimal codons encoding the same amino acid. As used herein, the term "synonymously substituted" refers to the replacement or substitution of one or more codons from a nucleic acid sequence with one or more synonymous codons. "Synonymous codons" refers to same-sense codons that do not alter the identity of the recombinant protein produced by a host cell. For example, UUU and UUC code for the same amino acid-phenylalanine. Most of the time, if the third nucleotide is the one with the mutation, it will result in coding for the same amino acid. This is called a synonymous mutation because, like a synonym in grammar, the mutated codon has the same meaning as the original codon and therefore does not change the amino acid.

In some embodiments, the synthetic nucleic acid sequence can be RNA, such as mRNA or in vitro transcribed mRNA, or DNA, such as cDNA. The synthetic nucleic sequence, such as RNA or DNA, can be provided in an RNA or DNA expression vector.

In other embodiments, the synthetic nucleic acid sequence can be ligated into an expression vector. A host cell can then be transfected with the expression vector. The transfected host cell can be cultured in a suitable culture media appropriate for the expression of a protein and the protein can be isolated.

For example, as shown in the graph of FIG. 2C, optimal or non-optimal codons in a nucleic acid sequence of interest can be identified. Next, one or more codons can be replaced with optimal or non-optimal synonymous codon(s) in the polynucleotide sequence of interest. The substituted polynucleotide sequence can then be inserted in a vector prior to transfection of a host cell in order to increase or decrease heterologous expression of a recombinant protein in host cell.

In some embodiments, the synthetic nucleic acid sequence with such modification(s) is capable of expressing the protein at a level that is at least about 10%, about 20%, about 25%, about 30%, about 40%, about 50%, about 60%, about 70%, about 80%, about 90%, about 100%, or more different (e.g., greater or less) compared to that expressed by the wild type nucleic acid sequence in an in vitro mammalian cell culture system under identical conditions.

The stability of mRNA with the replaced codons is directly proportional to the percentages of replaced optimal codons or non-optimal codons.

In some embodiments, one or more of the optimal codons of the wild type nucleic acid sequence can replaced with a non-optimal codon encoding the same amino acid as the replaced codon so that the synthetic nucleic acid sequence has less than about 50%, less than about 40%, less than about 30%, less than about 25%, less than about 20%, less than about 10%, or less than about 1% optimal codons. The replacement of the one or more optimal codons from the nucleic acid sequence with a non-optimal codon can decrease stabilization of mRNA transcribed from the nucleic acid sequence compared to the nucleic acid sequence prior to replacement.

In other embodiments one or more of the non-optimal codons is replaced with an optimal codon encoding the same amino acid as the replaced codon so that the synthetic nucleic acid sequence has more than about 50%, more than about 60%, more than about 70%, more than about 75%, more than about 80%, more than about 90%, more than about 95%, or more than about 99% about optimal codons. The replacement of the one or more non-optimal codons from the nucleic acid sequence with optimal codons can increase stabilization of mRNA transcribed from the nucleic acid sequence compared to the nucleic acid sequence prior to replacement.

As discussed above, substitution of optimal codons with synonymous, non-optimal codons results in dramatic mRNA destabilization, while the converse substitution significantly increases stability. Therefore, in some embodiments, the optimization of a nucleic sequence for heterologous expression in a host cell increases stabilization of mRNA transcribed from the optimized polynucleotide sequence compared to the original polynucleotide sequence. In other embodiments, the optimization of a nucleic sequence for heterologous expression in a host cell decreases stabilization of mRNA transcribed from the optimized polynucleotide sequence compared to the original polynucleotide sequence.

The optimized nucleic acids described herein may be recombinantly expressed by molecular cloning into an expression vector containing a suitable promoter and other appropriate transcription regulatory elements, and transferred into eukaryotic host cells to produce a recombinant protein of interest. Techniques for such manipulations are described in the art (Sambrook et al. Molecular Cloning: A Laboratory Manual; Cold Spring Harbor Laboratory Press, Cold Spring Harbor, N.Y., (1989); Current Protocols in Molecular Biology, Ausubel et al., Green Pub. Associates and Wiley-Interscience, New York (1988); Yeast Genetics: A Laboratory Course Manual, Rose et al., Cold Spring Harbor Laboratory, Cold Spring Harbor, N.Y., (1990), which are hereby incorporated by reference in their entirety).

Host cells for use in the preparation of heterologous recombinant proteins in a method described herein can include but are not limited to eukaryotic cells typically used in large-scale protein expression. Exemplary eukaryotic cells include but are not limited to yeast cells and mammalian cells. Yeast cells can include yeast is selected from the group consisting of: *Saccharomyces cerevisiae, Hansenula polymorpha, Pichia pastoris, Kluyvermyces fragilis, Kluveromyces lactis,* and *Schizosaccharomyces pombe.* Mammalian cells can include but are not limited to Chinese Hamster Ovary cells (CHO) cells, Human Embryonic Retinoblast (HER) cells, and Human Embryonic Kidney (HEK) cells. In some particular embodiments, the eukaryotic cell host is a yeast cell or a Chinese Hamster Ovary (CHO) cell.

Other embodiments relate to a method for preparing a synthetic nucleic acid encoding a protein expressed by a eukaryotic cell. The method can include identifying optimal and non-optimal codons in a nucleic acid encoding the protein, and replacing one or more of the optimal codons with a non-optimal codon encoding the same amino acid as the replaced codon or replacing one or more of the nonoptimal codons with an optimal codon encoding the same amino acid. The replacement of the one or more codons from the nucleic acid encoding the protein can modulate expression of the protein in the eukaryotic cell at least about 10%, about 20%, about 25%, about 30%, about 40%, about 50%, about 60%, about 70%, about 80%, about 90%, about 100%, or more compared to that expressed by the nucleic acid prior to replacement in an in vitro mammalian cell culture system under identical conditions.

Still other embodiments described herein relate to a method of modulating the expression of a recombinant protein in a host cell. The method can include identifying optimal and non-optimal codons in a nucleic acid sequence that encodes the protein. One or more of the optimal codons can then be replaced with a non-optimal codon encoding the same amino acid as the replaced codon or one or more of the non-optimal codons can be replaced with an optimal codon encoding the same amino acid. The host cell can be transfected with the nucleic acid with the replaced codon. The replacement of the one or more codons from the nucleic acid sequence can modulates expression of the recombinant protein in the host cell at least about 10%, about 20%, about 25%, about 30%, about 40%, about 50%, about 60%, about 70%, about 80%, about 90%, about 100%, or more compared to the nucleic sequence prior to replacement.

In some embodiments, the replacement of the one or more codons from the nucleic acid sequence increases expression of the recombinant protein in the host cell at least about 10%, about 20%, about 25%, about 30%, about 40%, about 50%, about 60%, about 70%, about 80%, about 90%, about 100%, or more compared to the nucleic acid sequence prior to replacement. The replacement of the one or more codons from the nucleic acid sequence can increase stabilization of mRNA transcribed from the nucleic acid sequence compared to the nucleic acid sequence prior to replacement.

In other embodiments, the replacement of the one or more codons from the nucleic acid sequence can decrease expression of the recombinant protein in the host cell at least about 10%, at least about 10%, about 20%, about 25%, about 30%, about 40%, about 50%, about 60%, about 70%, about 80%, about 90%, or more compared to the nucleic acid sequence prior to replacement. The replacement of the one or more codons from the nucleic acid sequence can decreases stabilization of mRNA transcribed from the nucleic acid sequence compared to the nucleic acid sequence prior to replacement.

In one exemplary embodiment, LSM8, a naturally occurring non-optimal mRNA can be synonymously substituted with one or more codons for greater optimality and heterologous expression (see FIG. 3E). In some embodiments, a naturally occurring mRNA can be synonymously substituted with one or more codons for lower optimality. In one exemplary embodiment, RPS20, a naturally occurring mRNA can be synonymously substituted with one or more codons for lower optimality resulting in a lower mRNA expression of RPS20 in yeast cells (see FIG. 3D).

Codon optimization methods described herein can be applied to any life science research area, allowing biologists to systematically enhance or reduce the expression of recombinant genes in a heterologous host organism.

In some embodiments, methods of the application can be used in large-scale protein expression. For example, methods of the present application can be used to manipulate codon optimality in order to produce more or less of a gene of interest for creating drugs, treating disease, etc. Well known molecular biology techniques can be applied to manipulate a polynucleotide encoding a gene to contain ideal codons and obtain the gene expression pattern that is most beneficial to a given application.

In certain embodiments, methods of the present disclosure can be used to enhance the expression of foreign genes in commonly used microbial cell factories such as *Saccharomyces cerevisiae* and *Pichia pastoris*. Therefore, the methods of the present disclosure can be used in any industry where it is desirable to improve the production of heterologous proteins in a particular host organism. As such, the methods of the present disclosure can be integrated into biopharmaceutical processes to improve the production of therapeutic protein drugs.

In some embodiments, methods of the present disclosure can be used to produce Human Recombinant insulin in *Saccharomyces cerevisiae* yeast cells. For example, a human proinsulin polynucleotide sequence can be optimized as described above prior to inclusion of the polynucleotide into a recombinant plasmid and subsequent transformation into a yeast host cell resulting in an increase of insulin protein expression by the host yeast cells.

In addition, in cases where metabolic engineering of cells is required, the methods of the present disclosure can be used to enhance the expression of the respective metabolic enzymes to alter biosynthetic pathways for biotechnological applications which can include biofuel production, biocatalysis and bioremediation.

In certain embodiments, the heterologous protein of interest expressed in a host cell is an antibody. Chinese Hamster Ovary cells (CHO) are commonly used for expression of recombinant proteins, including monoclonal antibodies. CHO cells are the predominant host used to produce therapeutic proteins. About 70% of all recombinant proteins produced today are made in CHO cells, including DUXB11, DG44 and CHOK1 lineages. The ability to grow to high density in serum-free suspension culture conditions, as well as to express and secrete proteins with the appropriate post-translational modifications (e.g., glycosylation), make CHO cells suitable for production of many antibodies or proteins intended for human therapeutic applications. Therefore, it is further contemplated that recombinant CHO cells transfected with an optimized polynucleotide sequence encoding high-, moderate- or low-expression genes described above can successfully grow in large-scale cultures of either adherent cells or suspension-adapted cells.

The present invention also relates to recombinant vectors and recombinant host cells, both prokaryotic and eukaryotic, which contain the optimized or non-optimized codon substituted nucleic acid molecules disclosed throughout this specification. In some embodiments, a stable cell line capable of heterologous expression in a host cell comprising an optimized polynucleotide described above is provided. The process for development of a stable cell line starts with expression vector construction and transfection. After being transfected with plasmids bearing for example, optimized polynucleotides encoding antibody light and heavy chain genes, as well as selectable marker or markers, cells can be screened for high productivity following growth recovery, serum-free suspension adaptation and amplification (if necessary) and clone selection.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example

Codon Optimality is a Major Determinat of mRNA Stability

In this Example, we show that codon optimality has a broad and powerful influence on mRNA stability in eukaryotic cells, such as yeast cells. First, global analysis of RNA decay rates reveals that mRNA half-life correlates with optimal codon content. Many stable mRNAs demonstrate a strong preference towards the inclusion of optimal codons within their coding regions, while many unstable mRNAs harbor non-optimal codons. Second, we demonstrate that substitution of optimal codons with synonymous, non-optimal codons results in a dramatic destabilization of the mRNA and that the converse replacement leads to a significant increase in mRNA stability. Third, we experimentally demonstrate an impact of codon optimality on ribosome translocation indicating that the effect on mRNA decay occurs through modulation of mRNA translation elongation. These findings indicate that transcript-specific translation elongation rate, as dictated by codon usage, is an important determinant of mRNA stability. Fourth, we observe tightly coordinated optimal codon content in genes encoding proteins with common physiological function. We hypothesize that this finding explains the previously observed similarity in mRNA decay rates for these gene families. Taken together, our data suggest that there is evolutionary pressure on protein coding regions to coordinate gene expression at the level of protein synthesis and mRNA decay.

Ribosomes are the Master Gatekeepers, Determining the Downstream Fate of Both Normal and Aberrant mRNAs As a final implication, our work suggests that co-translational mRNA surveillance by the ribosome is not only important to target aberrant mRNAs to rapid decay, but also to tune the degradation rates of normal mRNAs. In eukaryotes, aberrations in mRNAs lead to aberrant translation events such as premature termination, lack of translation termination, and ribosome stalling, which result in the accelerated turnover of the mRNA by the Nonsense-Mediated, Non Stop, and No-Go Decay pathways, respectively (Shoemaker and Green, 2012). We find here that codon usage within normal mRNAs also influences translating ribosomes and can have profound effects on mRNA stability.

Thus, the ribosome acts as the master sensor, helping to determine the fate of all mRNAs, both normal and aberrant, through modulation of its elongation and/or termination processes. The use of the ribosome as a sensor is ideal for protein-coding genes, whose primary function in the cell is to be translated. We suggest that a component of mRNA stability is built into all mRNAs as a function of codon composition. The elongation rate of translating ribosomes is communicated to the general decay machinery, which affects the rate of deadenylation and decapping. Individually, the identity of codons within an mRNA would be predicted to have a minute influence on overall ribosomal decoding; however, within the framework of an entire mRNA, we show that codon optimality can have profound effects on translation elongation and mRNA turnover. We therefore conclude that codon identity represents a general property of mRNAs and is a critical determinant of their stability.

Experimental Procedures

Yeast Strains and Growth Conditions

Unless indicated, all strains are based on BY4741. Cells were grown in standard synthetic medium (pH 6.5) supplemented with appropriate amino acids and sugars. All cells were grown at 24° C. and collected at midlog phase ($3 \times 10^7$ cells ml$^{-1}$).

Plasmids and Strain Construction

Reporter plasmids bearing native genes (LSM8, RPS20, HIS3 WT) were constructed by amplifying the native loci, adding restriction sites and several unique sites (to facilitate detection by northern probe) in the 3' UTR by site-directed mutagenesis, and inserting the construct into an expression vector. The reporters with altered optimality (LSM8 opt, RPS20 nonopt, HIS3 opt & non-opt) were constructed by synthesizing the DNA in multiple pieces, annealing and amplifying them, and then subcloning into an expression vector. These reporter plasmids were transformed into an rpb1-1 yeast strain. To construct the plasmids bearing the synthetic reporters, restriction sites were introduced into previously constructed plasmids bearing MFA2 and PGK1 under the control of a GAL1 UAS. The SYN ORFs were then synthesized and assembled as described for the altered reporters above. These reporters were transformed into a WT yeast strain.

Northern RNA Analysis and Sucrose Density Gradients

Northern RNA analysis of GAL-driven reporters and sucrose density gradients for polyribosome analysis was performed as previously described (Hu et al, 2009). For analysis of reporters in rpb1-1 was performed similarly to GAL, except cells were grown in media containing glucose and repression was achieved by shifting cells to 37° C. Ribosomal run-off experiments were performed similarly to normal polyribosome analysis, except cells were resuspended in media lacking glucose for 10 minutes before harvesting (Coller and Parker, 2005).

RNA-Seq rpb1-1 mutant cells (Nonet et al., 1987) were grown to mid-log phase at 24° C. and shifted to a non-permissive temperature of 37° C. Aliquots were collected over 60 minutes. RNA was then extracted, external controls were added, and two sets libraries were prepared from each using the Illumina TruSeq® Stranded Total RNA and mRNA library prep kits. The libraries were quantitated using an Agilent Bioanalyzer and sequenced on an Illumina HiSeq® 2000 using paired-end 100 bp reads with an index read. Sequencing data and the processed data for each gene are available at the Gene Expression Omnibus (www.ncbi.nlm.nih.gov/geo) under accession number GSE57385.

Alignment and Half-Life Calculation

Reads were aligned to the S. cerevisiae reference genome using bowtie (Langmead et al., 2009), with the unaligned reads then aligned to the sequences of the controls in the same way. Aligned reads were quantitated using cufflinks (Trapnell et al., 2010). Raw FPKM numbers were normalized to external controls, then fitted to single exponential decay curves to calculate the half-lives using the least absolute deviation method to minimize outlier effects. Data was then filtered to exclude dubious ORFs and transcripts with poor fit to the model. Bootstrapped confidence intervals were generated by using un-normalized residuals from the original data to generate simulated data sets.

Statistical Methods

The Codon occurrence to mRNA Stability Correlation coefficient (CSC) was determined by calculating a Pearson correlation coefficient between the frequency of occurrence of individual codons and the half-lives of the messages containing them. To determine the statistical significance, we categorized the CSC as either positive or negative and used a chi-squared test of association. For association between the categories of percent optimal codons and mRNA half-life, an ANOVA f-test with mRNA half-life on the log scale was used. To mitigate effects of base pair content of the genes, we randomly permuted the sequence and recalculated the test statistic for each of 10,000 permutations. The permutation p-value was calculated as the number of permuted data sets with a test of association stronger than the chi squared test in the original data. Statistical calculations were done using the R environment. Optimality percentages were calculated by generating a list of optimal and non-optimal codons as previously described (Pechmann and Frydman, 2013).

Plasmids and Strain Construction

The plasmids and oligonucleotides used in this study are listed in Supplementary Tables 3 and 4 respectively.

LSM8 & RPS20 reporters: To construct the base reporter plasmids bearing LSM8 (pJC663) and RPS20 (pJC666), DNA was amplified from the LSM8 locus with oJC2357/oJC2358 and from the RPS20 locus with oJC2366/oJC2367. Restriction sites were inserted by site-directed mutagenesis to facilitate further cloning. XhoI sites were introduced directly upstream of the start codon in both using oJC2415/oJC2416 and oJC2417/oJC2418 respectively. SphI sites were introduced directly downstream of the stop codon using oJC2431/oJC2432 and oJC2433/oJC2434. Several point mutations were introduced into the 3' UTRs to facilitate detection using oJC2435/oJC2436 and oJC2437/oJC2438 respectively. These were then cloned into pJC69 (Gietz and Sugino, 1988) to create pJC663, 666. The optimality-inverted plasmids (pJC667, 668 respectively) were constructed by synthesizing the ORF in two parts by annealing oJC2421/oJC2422 and amplifying with oJC2423/oJC2424 for LSM8 and annealing oJC2427/oJC2428 and amplifying with oJC2427/oJC2428 for RPS20. These inserts were cloned back into the XhoI/SphI sites of pJC663, 666. These reporters were transformed into yJC244 to make yJC1888-91.

SYN reporters: To construct the plasmids bearing the synthetic reporters, restriction sites were introduced directly before the start codon and after the stop codon of a PGK1-bearing plasmid (pJC296) as well as an MFA2-bearing plasmid (pJC312). Both of these plasmids are under the control of a GAL1 UAS. SpeI and XhoI sites were inserted into pJC296, using oJC2377/oJC2378 and oJC2379/oJC2380 respectively. XbaI and XhoI sites were introduced into pJC312, using oJC2381/oJC2382 and oJC2383/oJC2384 respectively. The SYN-opt sequence was synthesized as two complementary oligonucleotides (oJC2385/oJC2409), then annealed and digested with SpeI/XhoI, then ligated into similarly digested plasmids prepared as above to make the SYN-opt reporters with PGK1 context (pJC672) and MFA2 context (pJC674). The SYNnonopt oligonucleotides (oJC2386/oJC2410) were processed identically to generate the SYN-nonopt reporter with PGK1 context (pJC673) and MFA2 context (pJC675). These reporters were transformed into yJC151 to make yJC1892-95.

HIS3 reporters: For the HIS3 reporters, the endogenous reporter (pJC712) was made by amplifying the URA3 selectable marker from pJC390 with oJC2508/2509 and inserting it into the cloning site of pJC387, which already contained the HIS3 ORF under the control of its native promoter. This was transformed into yJC151 to make yJC2031 and into yJC1883 to make yJC2033. The non-optimal ORF was synthesized by annealing 4 oligonucleotides (oJC2500-3), then amplifying with oJC2518/oJC2519, and replacing the existing ORF of the pJC387 plasmid using PacI/AscI to make pJC710. Selectable marker URA3 was then added as described above to make pJC711. This was transformed into yJC151 to make yJC2030 and into yJC1883 to make yJC2032. The optimal ORF was constructed by annealing 4 oligonucleotides (oJC2605-8), amplifying with pJC2611/2612, and then replacing the ORF of pJC711 using PacI/AscI to make pJC716. This was transformed into yJC151 to make yJC2088 and into yJC244 to make yJC2090. FLAG-tagged versions were produced by introducing the FLAG tag via site-directed mutagenesis into pJC711 using oligonucleotides oJC2620/2621 to make pJC719 and into pJC716 using oligonucleotides oJC2622/2623 to make pJC720. These were transformed into yJC151 to make yJC2135 and yJC2137 respectively. All of the HIS3 constructs were designed to retain a short invariant region in the ORF (positions 337-359), which was used for detection by northern oligonucleotide probe oJC2564.

Northern RNA Analysis

Northern RNA analysis was performed essentially as previously described (Hu et al., 2009). Briefly, for analysis of the SYN reporters, cells carrying the SYN reporters were grown in 2% galactose, 1% sucrose synthetic media and collected at mid-log phase. Transcription repression was achieved by resuspending collected cells in media containing 4% glucose. After transcriptional repression, cell aliquots were removed, total RNA was isolated by (30 mg) was analyzed by electrophoresis through 1.4% formaldehyde agarose gel or 6% denaturing polyacrylamide gel. For analysis of LSM8, RPS20, and HIS3 reporters, rpb1-1 shut-offs were performed as described below in the first paragraph of the RNA-seq section, then loaded onto 1.4% formaldehyde agarose gels instead of library construction and following steps.

Northern analyses were performed using oligonucleotide radiolabelled with T4 PNK. Specifically, the LSM8 reporters were detected using oJC2450, RPS20 with oJC2451, HIS3 with oJC2564, and SYN RNAs with oJC168. Northern signal quantitation was performed using ImageQuant software.

Polyribosome Analysis

Sucrose density gradients for polyribosome analysis were performed essentially as described previously (Hu et al., 2009). Specifically, cells were grown until mid-log phase (OD600=0.4-0.45) at 24° C. in synthetic media with the appropriate amino acids and 2% glucose. For glucose deprivation experiments, cells were centrifuged and resuspended in media with or without glucose for 10 min before harvesting. All cells were treated with cycloheximide to a final concentration of 100 μg ml$^{-1}$ and collected by centrifugation. Cell pellets were lysed in buffer (10 mM Tris, pH 7.4, 100 mM NaCl, 30 mM MgCl$_2$, 1 mM DTT, 100 μg ml$^{-1}$ cycloheximide) by vortexing with glass beads, and cleared using the hot needle puncture method followed by centrifugation at 2,000 rpm for 2 min at 4° C. After centrifugation of the supernatants at 29,000 r.p.m. for 10 min with a TLA 120.2 rotor, Triton X-100 was added to a final concentration of 1%. Sucrose gradients were made on a Biocomp gradient maker and were 15-45% weight/weight (sucrose to buffer (50 mM TrisAcetate pH 7.0, 50 mM NH$_4$Cl, 12 mM MgCl$_2$, 1 mM DTT)). 10 units (OD260) of cell lysate were loaded onto each gradient. Gradients were centrifuged at 41,000 r.p.m. for 2 h and 26 min at 4° C. in a Beckman SW-41Ti rotor and fractionated using a Brandel Fractionation System and an ISCO UA-6 ultraviolet detector. Fractions were precipitated overnight at −20° C. using 2 volumes 95% ethanol. RNA/protein was pelleted at 14,000 rpm for 30 min, then pellets were resuspended in 500 μL LET (25 mM Tris pH 8.0, 100 mM LiCl, 20 mM EDTA) with 1% SDS. Fractions were then extracted once with phenol/LET, once with phenol/chloroform/LET, and then were precipitated with one-tenth volume of 7.5 M $CH_3COONH_4$ and 2 volumes 95% ethanol. After centrifugation at 14,000 rpm for 20 min, pellets were washed once with 700 μL 75% ethanol, air dried, and resuspended in 1×LET. Half of each sample was loaded on 1.4% agarose-formaldehyde gels and Northern analysis carried out as above. For HIS3, northern blots of RNA from cells without stress were probed with oligonucleotide oJC2564 and northern blots of RNA from cells with stress were probed with probes generated by radiolabeled asymmetric PCR for increased sensitivity. For RPS20, blots were probed with oligonucleotide oJC2632. For LSM8, an asymmetric PCR probe was used for increased sensitivity. To generate the asymmetric PCR probes, plasmids pJC711 and pJC716 were used as templates to amplify non-optimal and optimal HIS3 sequences, respectively, in a first PCR using oJC2540 and oJC2541 and Phusion Taq polymerase (BioLabs). The PCR products were run on 1% agarose gel and the single amplicons were extracted using a GenElute Gel extraction kit (Sigma) and resuspended in 30 μL of water. 4 μL were added to a final 50 μL PCR mix containing dATP, dGTP, dTTP (200 μM each), dCTP (3 μM), the reverse primer oJC2564 (HIS3 ORF, 1 μM), 50 μCi of [α-32P]dCTP (3000 Ci/mmol; 10 μCi/μL) and 5 units of Taq polymerase. After denaturation at 94° C. for 5', asymmetric amplification was performed for 40 cycles (15 sec at 94° C., 30 sec at 58° C., 30 sec at 72° C.) followed by 10 min at 72° C. The obtained radiolabelled probes were purified on Micro Bio-Spin 6 Chromatography Columns (BioRad) following the manufacturer's instructions. For LSM8, the PCR template was generated using oligonucleotides oJC2357 and oJC2358. The reverse primer for the asymmetric PCR was oJC2633. Blots were pre-hybridized 1 h at 42° C. in 50% formamide, 5×SSC, 1×Denhardt's, 0.5 mg/mL salmon sperm DNA, 10 mM EDTA and 0.2% SDS, and probed with the optimal or non-optimal single-stranded probes generated by asymmetric PCR overnight at 42° C. in the same buffer. They were washed twice for 5 min at room temperature in 2×SSC, 0.1% SDS, and once for 45 min at 50° C. in 0.1×SSC, 0.1% SDS, and then placed on phosphorimager screens for overnight exposure.

RNA-Seq rpb1-1 mutant cells (Nonet et al., 1987) (yJC244) were grown to mid-log phase at 24° C. as described above. To achieve transcriptional repression, cells were shifted to 37° C., then cell aliquots were removed and isolated total RNA was used for library construction. 10 time points were collected over 60 minutes, including an initial aliquot at time 0 collected before the temperature shift. Total RNA libraries were then prepared using the Illumina TruSeq Stranded Total RNA library prep kit. The starting material consisted of 1 μg of total RNA and 1 ng of ERCC Phage NIST spike-ins. Poly(A)+RNA libraries were prepared using the Illumina TruSeq Stranded mRNA library prep kit. The starting material for these libraries consisted of 4 μg of RNA and 1 ng of ERCC Phage NIST spike-ins. The libraries were quantitated using an Agilent Bioanalyzer and sequenced on an Illumina HiSeq2000 using paired-end 100 bp reads with an index read.

Alignment and Half-Life Calculation

Reads were aligned to the SacCer2 S. cerevisiae reference genome using Bowtie v0.12.7 (Langmead et al., 2009) using the parameters '–m 1–v 2–p 8'. The remaining unaligned reads were then aligned to a reference file containing the sequences of the spike-in controls using the same parameters. The aligned reads were then converted into bam format and indexed using samtools v0.1.18 (Li et al., 2009). Gene FPKM values were calculated with Cufflinks v1.3.0 (Trapnell et al., 2010) using default parameters and a gtf file of the SGD gene annotation downloaded from the SacCer2 UCSC browser. The raw FPKM numbers were then normalized to the number of reads aligning to the spike-ins to adjust for the amplification resulting from a smaller pool of mRNA at later time points.

To estimate the half-life for each gene, we normalized each of the expression levels for each gene and each time series to the initial expression level. We then fit an exponential decay curve to the data by minimizing the sum of the absolute residuals for each gene. We filtered the list to exclude dubious and unverified ORFs, genes for which the average absolute residual was greater than 0.14, and genes which had an estimated half-life longer than the measured time course. To get a very rough idea of the variability in our estimates of the gene half-lives we performed a bootstrap type procedure. The un-normalized residuals from the original data were resampled for each gene and added to the un-normalized fitted curve values to repeatedly simulate new sample data sets. The 95% confidence intervals were based on the 2.5% and 97.5% quantiles of the half-life estimates calculated from the simulated data sets.

Statistical Methods

The Codon occurrence to mRNA Stability Correlation coefficient (CSC) was determined by calculating a Pearson correlation coefficient between the frequency of occurrence of individual codons and the half-lives of the messages containing them (FIG. 1A). To determine the statistical significance of the association between codon optimality and the CSC (FIGS. 2A, C), we first categorized the CSC as either positive or negative. We then used a chi-squared test of association. We also used linear regression (FIG. 2D). Similarly, to look at association in between the categories of optimal codon content and mRNA half-life (FIG. 3F), we used an ANOVA f-test with mRNA half life on the log scale.

Any test of association between codon optimality and transcript stability may show artificial statistical significance due to confounding with the base pair content of the genes. To help mitigate this possibility, for each test statistic, we randomly permuted the base pairs of the genes and recalculated the test statistic for each of 10,000 permutations. We calculated the base pair permutation p-value as the number of permuted data sets with a test of association stronger than the chi-squared test in the un-permuted data. Statistical calculations were done using the R environment. Percent optimal codon values were calculated by generating a list of optimal and non-optimal codons as previously described.

Heat Map Generation

For all mRNA with reliable half-lives, rates of usage of each of the 61 codons was calculated by using an in-house perl script. These values were then input into an Excel spreadsheet, assigned ranks using the RANK.AVG function, and then exported to a tsv file. These were then evaluated using a Spearman distance metric and clustered using k-means clustering in Cluster3. The clustered output was visualized and color coded using the log-scale option of Java Treeview.

Results

Measuring global mRNA decay rates using methods that either enrich for polyA+ RNA from total RNA samples and/or synthesize complementary DNA (cDNA) using oligonucleotides annealed to the poly(A) tail may fail to capture important information for several reasons. Although it is firmly established that deadenylation is the rate limiting step in mRNA turnover, we and others have observed that specific mRNAs persist in cells as "stable" deadenylated species. For such transcripts, decapping and subsequent decay is delayed and decapping becomes the rate defining step for mRNA degradation. Moreover, some mRNAs may contain structures that impede poly(A) tail function. Lastly, since the process of deadenylation converts an mRNA species from one that can be efficiently captured by oligo dT to one that cannot, the overall level of information gained may vary with the level of poly(A) enrichment achieved in the protocol used. With this in mind, we sought to determine how prevalent these phenomena are on a transcriptome-wide level. For this purpose, we performed a time course after inactivation of RNA polymerase II. At each time point, libraries were prepared from either oligo-dT selected mRNAs or rRNA-depleted whole cell RNA and subjected to Illumina sequencing. This approach allowed us to compare poly(A) half-lives (oligo dT) with total mRNA decay rates (rRNA depleted; FIG. 1A). Remarkably, the vast majority (92%) of transcripts for which we could confidently calculate half-lives (3969) had longer half-lives when the rRNA depleted libraries were analyzed relative to the half-lives determined from poly(A) selected libraries (FIGS. 1B and C). It is important to note that not all of these transcripts exist as deadenylated RNAs since mRNAs with short poly(A) tails will not bind oligo dT. These data indicate that mRNA half-lives determined by oligo dT selection give highly skewed values. For example, the ADH1 mRNA had a calculated half-life of 4.2 minutes when determined from poly(A) selected RNA and a 31.7 minute half-life when determined from rRNA depleted RNA.

With this data in hand we attempted to identify sequence motifs that might dictate stability or instability, without success. Following up on previous observations that inclusion of ten consecutive rare codons in the open reading frames of an otherwise stable mRNA caused a dramatic decrease in stability, we inspected our transcriptome-wide mRNA half-life data to determine whether codon content within ORFs could affect mRNA stability. To do so, we determined if mRNAs enriched in any individual codon demonstrated greater or lesser stability. We defined mRNAs as stable if they have a half-life greater than 2-fold longer than the average (~20 min), and unstable if they have a half-life less than half of the average (~5 min). For each codon, we calculated a correlation between the frequency of occurrence of that codon in mRNAs and the stabilities of the mRNAs. Occurrences of a codon were compared to the half-life for each mRNA and a Pearson correlation calculation was used to generate an R-value (graphically represented for sample codons in FIG. 8E). We refer to this metric as the Codon occurrence to mRNA Stability Correlation coefficient (CSC). The CSC values for all codons were then compared to each other (FIG. 2A). Strikingly, it was observed that some codons preferentially occurred in stable mRNAs while others occurred preferentially in unstable mRNAs (overall p-value=1.496e−14, permutation p-value $<10^{-4}$). For example, the GCT alanine codon was highly enriched in stable transcripts as defined by our RNA-seq analysis, while its synonymous codons, GCG and GCA were preferentially present in unstable transcripts (FIG. 2A). Approximately one-third of all codon triplets were over-represented in stable mRNAs, while the remaining two-thirds appeared to predominate in unstable mRNAs. As a consequence of the large dataset and significance of the observed correlation, these data strongly suggest that codon usage influences mRNA degradation rates.

Strikingly, codons associated with stable or unstable mRNAs nearly perfectly mirrored their assignment as optimal or non-optimal, respectively (FIG. 2C). Direct comparison between our CSC metric and tAI revealed very good overall agreement between these values (FIG. 2D; R=0.753, p-value=2.583e−12, permutation p-value <10−4). Importantly, the relationship between optimal codon content and mRNA half-life is independent of the method used to determine half-life. We repeated our analysis of codon usage vs. mRNA half-life using mRNA decay rates. These data were obtained with a steady state approach calculation using metabolic labeling that minimally perturbs the cell and is completely distinct from our method. Both datasets show a similar and striking correlation between optimal codon content and mRNA decay rate.

To determine if the codon optimality correlation was possibly masking other features that might actually be determining mRNA half-life (e.g., sequence content, GC percentage, or secondary structure), we reanalyzed our data after computationally introducing +1 and +2 frameshifts. In the analysis of these frameshifted ORFs, the correlation between codon content and stability completely disappears, thus eliminating other variables as determinative (FIG. 2E; R=−0.127, p-value=0.3303, permutation p-value=0.8847 and FIG. 2F; R=−0.288, p-value=0.0242, permutation p-value=0.0012).

Stable and Unstable mRNAs Demonstrate Different Optimal Codon Content

As shown above, computational analysis of our global mRNA stability data revealed a relationship between codon occurrence and mRNA half-life. These data indicate that either particular codons alter stability or overall codon content within an mRNA works collectively on stability. To evaluate the relationship between optimal codon content and decay rate on the level of individual transcripts, codon usage was mapped across all individual transcripts. Cluster analysis revealed that different mRNAs are biased towards using different types of codons. The overall result is not surprising, as codon bias has been well studied; however, the pattern of codon usage demonstrates that certain classes of mRNAs predominately use either optimal or non-optimal codons (FIGS. 3A and B) and that this usage correlates with the overall transcript stability (FIG. 3C). Closer inspection of several stable mRNAs revealed that these transcripts were not enriched in any particular codon, but an overwhelming proportion (>80%) of codons fell into the category of optimal (FIG. 3D). By contrast, individual unstable mRNAs were found to be enriched (60% or greater) in non-optimal codons (FIG. 3E). These analyses demonstrated that in this set of mRNAs, the stable mRNAs are biased towards harboring predominately optimal codons and the unstable mRNAs are enriched in nonoptimal codons, though the specific codon identities vary between individual transcripts.

Extending this analysis to the level of the whole transcriptome, a correlation between optimal codon content and mRNA stability was observed when the proportion of optimal codons within an mRNA was evaluated by percentiles. Specifically, mRNAs with less than 40% optimal codons were typically found to be unstable, with a median half-life of 5.4 minutes. In contrast, mRNAs with 70% optimal codon content or greater were found to be stable, with a median half life of 17.8 minutes (FIG. 3F).

Optimal Codon Content Directly Influences mRNA Decay Rate

To experimentally validate the relationship observed in the computational analysis, we evaluated the effects on stability of altering the percentage of optimal codons within an mRNA. We modified the codon content of the unstable LSM8 mRNA (half-life=4.65 min) by making synonymous optimal substitutions in 52 of its 60 nonoptimal codons. Similarly, we replaced the majority of optimal codons (108 of 113) within the coding region of the stable RPS20 mRNA (half-life=25.3 min) with synonymous, non-optimal codons. This methodology ensured that the polypeptides encoded by these sequences were unchanged from the native form. Moreover, the substitutions were selected to avoid significantly altering the GC content of the coding region or introducing any predicted RNA secondary structure (data not shown). Northern blot analysis of these mRNAs after transcriptional inhibition revealed that alteration of the codons within these two transcripts resulted in dramatic changes in their stability. Specifically, the half-life of LSM8 mRNA was increased greater than 7-fold as a consequence of the conversion of non-optimal codons into synonymous optimal codons in its ORF (half-life=18.7 min; FIG. 4A). In contrast, substitution of non-optimal for optimal codons within the stable RPS20 mRNA resulted in a sharp (10 fold) reduction in its stability (half-life=2.5 min; FIG. 4B). These data demonstrate that identity of codons within an mRNA can strongly influence stability, and that optimal codon content contributes significantly to determining the rate of mRNA decay in vivo.

To further examine the relationship between optimal codon content and mRNA stability, we generated two synthetic open reading frames which encode identical 59 amino acid polypeptides but differ in the optimality at each codon (SYN reporters; FIGS. 10A, B, and C). We introduced the synthetic ORFs into a reporter bearing the 5' and 3'UTRs of MFA2, a well studied mRNA which is rapidly degraded in the cell (half-life=3.0 min), a phenomenon shown to be mediated, in part, by elements encoded within its 3'UTR. We also introduced the synthetic ORFs into a reporter with the 5' and 3' UTRs of PGK1, a well characterized and stable mRNA (half-life=25 min; Muhlrad et al., 1995). When stability of the four reporter mRNAs was measured by transcriptional shut-off analysis, the transcripts encoding the optimal SYN ORF were found to be significantly more stable (~4-fold) than their counterparts bearing the non-optimal codons (FIG. 4C). Importantly, degradation of both the optimally and non-optimally encoded SYN reporter mRNAs was determined to occur through the deadenylation-dependent decapping pathway used to degrade the majority of endogenous mRNAs in yeast, and was not mediated by any of the three pathways known to target aberrant mRNA. High-resolution northern analysis of the decay of these mRNAs confirmed that the rates of both deadenylation and decapping, the regulated steps in the normal decay pathway, were affected as a consequence of changes in codon composition within the reporter ORFs. These data demonstrate that optimal codon content is a critical determinant of mRNA stability influencing both the rate of deadenylation and decapping during turnover of the mRNA independently of 5' and 3' UTRs, which can act in parallel to stabilize or destabilize the mRNA.

Optimal Codon Content Influences Translational Efficiency

To evaluate the influence of codon optimality on mRNA translation efficiency in vivo, we generated three new reporters that differ in optimal codon content but do not differ in amino acid sequence. Specifically, we engineered the ORF of the HIS3 gene to contain either all optimal (HIS3 opt) or all non-optimal codons (HIS3 non-opt), with the wild-type HIS3 gene providing an intermediate point at 43% optimal codons (FIG. 5A). The HIS3 gene was chosen because it has a relatively long ORF (220 amino acids) compared to our other synonymous mutation constructs, allowing us to effectively monitor ribosome association by sucrose density gradients (see below). We then determined the mRNA decay rate of the three HIS3 constructs by transcriptional shutoff analysis using an rpb1-1 strain. Consistent with our previous results, it was observed that changing optimal codon content produced a dramatic effect on mRNA half-life (FIG. 5B). Notably, the effect on HIS3 mRNA decay matched the percent of optimal codons used. The half-life of the optimal construct (half-life >60 min) was much greater that of the WT construct (half-life=9.5 min) whose half-life was markedly greater than the nonoptimal construct (half-life=2.0 min). Thus, we can achieve a full range of mRNA halflives in yeast without altering protein sequence or flanking sequences by changing optimal codon content.

We hypothesized that codon optimality should influence translation elongation. We tested this hypothesis using two approaches. First, we monitored the protein output from the HIS3 optimal construct vs. the HIS3 non-optimal construct by western blot, and then normalized the protein expression to the mRNA levels, as determined by northern blot. We observed that the non-optimal construct had four-fold less protein output than the optimal construct (FIG. 5C). Second, we evaluated the ribosome density on the HIS3 mRNA constructs. Ribosome density was monitored using sucrose gradients, followed by fractionation and northern blotting of the isolated fractions. Critically, it was observed that the ribosome occupancy was nearly identical for all three HIS3 reporter mRNAs (FIG. 5D). Thus, we show that a four-fold decrease in protein output, in conjunction with nearly identical localization within a polyribosome, suggests a decrease in ribosome translocation rate on the non-optimal construct as compared to the optimal.

Optimal Codon Content Impacts Ribosome Translocation

To directly determine whether ribosomes translocate slower on mRNAs containing non-optimal codons vs. optimal codons, we monitored ribosomal run-off of these two reporters. To do this, we blocked translational initiation by depriving cells of glucose for 10 minutes. Glucose deprivation results in rapid inhibition of translational initiation and thus bulk polyribosomes are lost by run-off (FIG. 6A vs. C). To monitor ribosomal run-off, we extracted mRNA-ribosome complexes before and after glucose deprivation, separated the material with a sucrose gradient, collected fractions, and monitored the presence of the HIS3 mRNAs in each fraction by northern analysis. Importantly, under normal conditions the ribosome occupancy of the HIS3 opt and non-opt constructs was determined to be similar (FIG. 6B); however, upon induction of ribosome run-off, a large fraction of the optimal construct mRNA relocated to the top of the gradient in the ribosome-free area, while the HIS3 non-opt mRNA remained largely associated with polyribosomes (FIG. 6D). We extended this analysis to two endogenous mRNA transcripts that differ dramatically in codon optimality, LSM8 (45% optimal codons) and RSP20 (92% optimal codons). Notably, the endogenous LSM8 mRNA was retained on polyribosomes following inhibition of translational initiation, while the RPS20 mRNA dissociated efficiently. We propose that the difference in retention is due to more efficient ribosome translocation on messages with high optimal codon content. Thus, the retention of the mRNAs bearing predominantly non-optimal codons in polyribosomal fractions indicates that codon optimality can impact the rate of ribosome translocation directly.

Precision in Gene Expression is Achieved Through Coordination of Optimal Codon Content A previous analysis of mRNA stability in yeast revealed that the decay rates of some mRNAs encoding proteins that function in the same pathway or are part of the same complex were similar. Turnover of individual mRNAs appears to be based on the physiological function and cellular requirement of the proteins they encode. We hypothesized that modulation of optimal codon content may provide the mechanism for the cell to coordinate the metabolism of transcripts expressing proteins of common function. We assessed codon usage for genes whose protein products function in common pathways and/or complexes. We observed that mRNAs encoding the enzymes involved in glycolysis (n=10) had a similar and extraordinarily high proportion of optimal codons (mean=86%; FIG. 7A). These transcripts were determined to be stable both previously and in our genome-wide analysis (median half-life=43.4 min; Wang et al., 2002). In contrast, mRNAs encoding polypeptides involved in pheromone response in yeast cells (n=14) were all unstable (median half-life=5.6 min; Wang et al., 2002) and harbored an average of only 43% optimal codons (FIG. 7A). Our analysis revealed that other groups of transcripts behave similarly. The stable large and small cytosolic ribosomal subunit protein mRNAs (n=70 and 54, respectively; median half-life=18.9 min and 20.2 min, respectively) demonstrated an average optimal codon content of 89% and 88% respectively, but mRNAs that encode ribosomal proteins functioning in the mitochondria are unstable (n=42; median half-life=4.8 min), consistent with the observation that they have 45% optimal codon content. (FIGS. 7A and B). Other families of genes that have similar decay rates include those whose protein products are involved in ribosomal processing, tRNA modification, the TCA cycle, RNA processing, and components of the translational machinery (FIG. 7 and data not shown). These data provide evidence that transcripts expressing proteins of related function are coordinated at the level of optimal codon content as well as decay rate, suggesting that these genes may have evolved specific codon contents as a mechanism to facilitate precise synchronization of expression based on their function in the cell.

From the above description of the invention, those skilled in the art will perceive improvements, changes and modifications Such improvements, changes and modifications are within the skill of the art and are intended to be covered by the appended claims. All publications, patents, and patent applications cited in the present application are herein incorporated by reference in their entirety.

Having described the invention, the following is claimed:

1. A synthetic nucleic acid which encodes a protein in a mammalian host cell, wherein at least one optimal or non-optimal codon in a wild type nucleic acid encoding the protein has been replaced respectively with one or more non-optimal codons or optimal codons encoding the same amino acid, the synthetic nucleic acid being capable of expressing the protein at a level that is at least about 10% different compared to that expressed by the wild type nucleic acid in an in vitro mammalian cell culture system under identical conditions, and wherein the optimal codons are selected from the group consisting of gct (Alanine), ggt (Glycine), gtc (Valine), ttg (Leucine), gtt (Valine), cca (Proline), act (Threonine), tct (Serine), tcc (Serine), gaa (Glutamic Acid), cgt (Arginine), caa (Glutamine), att (Isoleucine), aga (Arginine), and tgt (Cysteine); and the non-optimal codons are selected from the group consisting of ggc (Glycine), tgg (Tryptophan), atg (Methionine), tgc (Cysteine), ccc (Proline), gtg (Valine), cgc (Arginine), gag (Glutamic Acid), cag (Glutamine), agc (Serine), and ctg (Leucine);

wherein the replacement of one or more codons from the nucleic acid sequence with one or more optimal codons increases stabilization of mRNA and mRNA half-life or with one or more non-optimal codons decreases stabilization of mRNA and mRNA half-life transcribed from the nucleic acid sequence compared to the nucleic acid sequence prior to replacement.

2. The synthetic nucleic acid sequence of claim 1, wherein the synthetic nucleic sequence is capable of expressing the protein at a level which is at least about 50% different compared to that expressed by the wild type nucleic acid in an in vitro mammalian cell culture system under identical conditions.

3. The synthetic nucleic acid sequence of claim 1, wherein the synthetic nucleic sequence is capable of expressing the protein at a level which is at least about 75% different compared to that expressed by the wild type nucleic acid in an in vitro mammalian cell culture system under identical conditions.

4. The synthetic nucleic acid sequence of claim 1, wherein one or more of the optimal codons is replaced with a non-optimal codon encoding the same amino acid as the replaced codon so that the synthetic nucleic acid sequence has less than about 40% optimal codons.

5. The synthetic nucleic acid sequence of claim 1, wherein one or more of the non-optimal codons is replaced with an optimal codon encoding the same amino acid as the replaced codon so that the synthetic nucleic acid sequence has more than about 70% optimal codons.

6. The synthetic nucleic acid of claim 1, wherein the mammalian cell is a CHO (Chinese Hamster Ovary) cell.

7. The synthetic nucleic acid of claim 1, comprising in vitro transcribed mRNA.

8. The synthetic nucleic acid of claim 1, comprising DNA.

9. An expression vector comprising the synthetic nucleic acid of claim 1.

10. The expression vector of claim 9, being a mammalian expression vector.

11. A method of modulating the expression of a recombinant protein in a mammalian host cell, the method comprising:

identifying optimal and non-optimal codons in a nucleic acid sequence that encodes the protein, replacing one or more of the optimal codons with a non-optimal codon encoding the same amino acid as the replaced codon or replacing one or more of the non-optimal codons with an optimal codon encoding the same amino acid, and transfecting the mammalian host cell with the nucleic acid with the replaced codon, wherein the replacement of the one or more codons from the nucleic acid sequence modulates expression of the recombinant protein in the host cell at least about 10% compared to the nucleic sequence prior to replacement, and wherein the optimal codons are selected from the group consisting of gct (Alanine), ggt (Glycine), gtc (Valine), ttg (Leucine), gtt (Valine), cca (Proline), act (Threonine), tct (Serine), tcc (Serine), gaa (Glutamic Acid), cgt (Arginine), caa (Glutamine), att (Isoleucine), aga (Arginine), and tgt (Cysteine); and the non-optimal codons are selected from the group consisting of ggc (Glycine), tgg (Tryptophan), atg (Methionine), tgc (Cysteine), ccc (Proline), gtg (Valine), cgc (Arginine), gag (Glutamic Acid), cag (Glutamine), agc (Serine), and ctg (Leucine);

wherein the replacement of one or more codons from the nucleic acid sequence with one or more optimal codons increases stabilization of mRNA and mRNA half-life or with one or more non-optimal codons decreases stabilization of mRNA and mRNA half-life transcribed from the nucleic acid sequence compared to the nucleic acid sequence prior to replacement.

12. The method of claim 11, wherein the replacement of the one or more codons from the nucleic acid sequence increases expression of the recombinant protein in the host cell at least about 10% compared to the nucleic acid sequence prior to replacement.

13. The method of claim 12, wherein the replacement of the one or more codons from the nucleic acid sequence increases stabilization of mRNA transcribed from the nucleic acid sequence compared to the nucleic acid sequence prior to replacement.

14. The method of claim 11, wherein the replacement of the one or more codons from the nucleic acid sequence decreases expression of the recombinant protein in the host cell at least about 10% compared to the nucleic acid sequence prior to replacement.

15. The method of claim 14, wherein the replacement of the one or more codons from the nucleic acid sequence decreases stabilization of mRNA transcribed from the nucleic acid sequence compared to the nucleic acid sequence prior to replacement.

16. The method of claim 11, wherein the mammalian host cell is a CHO (Chinese Hamster Ovary) cell.

\* \* \* \* \*